US011723576B2

United States Patent
Rubin et al.

(10) Patent No.: US 11,723,576 B2
(45) Date of Patent: Aug. 15, 2023

(54) DETECTING ATRIAL FIBRILLATION USING SHORT SINGLE-LEAD ECG RECORDINGS

(71) Applicant: KONINKLIJKE PHILIPS N.V., Eindhoven (NL)

(72) Inventors: Jonathan Rubin, Cambridge, MA (US); Saman Parvaneh, Cambridge, MA (US); Asif Rahman, Cambridge, MA (US); Bryan Conroy, Cambridge, MA (US); Saeed Babaeizadeh, Arlington, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 418 days.

(21) Appl. No.: 16/641,824

(22) PCT Filed: Sep. 18, 2018

(86) PCT No.: PCT/EP2018/075113
§ 371 (c)(1),
(2) Date: Feb. 25, 2020

(87) PCT Pub. No.: WO2019/057676
PCT Pub. Date: Mar. 28, 2019

(65) Prior Publication Data
US 2020/0205687 A1     Jul. 2, 2020

Related U.S. Application Data

(60) Provisional application No. 62/561,253, filed on Sep. 21, 2017.

(51) Int. Cl.
*A61B 5/361*     (2021.01)
*G16H 50/20*     (2018.01)
(Continued)

(52) U.S. Cl.
CPC .............. *A61B 5/361* (2021.01); *A61B 5/339* (2021.01); *A61B 5/35* (2021.01); *A61B 5/7267* (2013.01); *G16H 50/20* (2018.01)

(58) Field of Classification Search
CPC ........... A61B 5/361; A61B 5/35; A61B 5/339; A61B 5/7267; G16H 50/20
See application file for complete search history.

(56) References Cited

U.S. PATENT DOCUMENTS

2011/0282227 A1   11/2011   Zhang
2013/0197380 A1   8/2013    Oral
(Continued)

OTHER PUBLICATIONS

January, C.T. et al., "2014 AHA/ACC/HRS guideline for the management of patients with atrial fibrillation," vol. 64, No. 21, 2014.
(Continued)

*Primary Examiner* — Michael W Kahelin
*Assistant Examiner* — Naveed R. Kolia

(57) ABSTRACT

A non-transitory computer-readable medium stores instructions readable and executable by at least one electronic processor (20) to perform an atrial fibrillation (AF) detection method (100). The method includes: generating a time-frequency representation of an electrocardiogram (ECG) signal acquired over a time interval; processing the time-frequency representation using a neural network (NN) (32) to output probabilities for rhythms of a set of rhythms including at least atrial fibrillation; assigning a rhythm for the ECG signal based on the probabilities for the rhythms of the set of rhythms output by the neural network; and controlling a display device (24) to display the rhythm assigned to the ECG signal.

13 Claims, 3 Drawing Sheets

(51) Int. Cl.
*A61B 5/00* (2006.01)
*A61B 5/35* (2021.01)
*A61B 5/339* (2021.01)

(56) References Cited

U.S. PATENT DOCUMENTS

| | | | |
|---|---|---|---|
| 2015/0190096 A1* | 7/2015 | Zong | A61B 5/14532 600/301 |
| 2016/0000349 A1 | 1/2016 | Sullivan | |
| 2017/0156592 A1 | 6/2017 | Fu | |
| 2018/0240235 A1* | 8/2018 | Mazo | G06N 3/04 |
| 2019/0192110 A1 | 6/2019 | Parvaneh et al. | |
| 2019/0328243 A1* | 10/2019 | Nemati | G16H 50/20 |

OTHER PUBLICATIONS

Huang, G. et al., "Densely connected convolutional networks," arXiv:1608.06993v5 [cs.CV] Jan. 28, 2018.

Tsipouras, M.G. et al., "Classification of atrial tachyarrhythmias in electrocardiograms using time frequency analysis", Computers in Cardiology, 2004 Chicago, IL, Sep. 19-22, 2004, pp. 245-248.

Ortigosa, N. et al., "Classification of atrial fibrillation episodes using short ECG segments", IEEE-EMBS International Conference on Biomedical and Health Informatics (BHI), IEEE, (Jun. 1, 2014), pp. 569-572.

Guler, I. et al., "ECG beat classifier designed by combined neural network model", Pattern Recognition, Elsevier, GB, vol. 38, No. 2, (Feb. 1, 2005), pp. 199-208.

Potes, C. et al., "Ensemble of feature-based and deep learning-based classifiers for detection of abnormal heart sounds," in Computing in Cardiology Conference (CinC), 2016, 2016, pp. 621-624.

Rubin, J. et al., "Recognizing Abnormal Heart Sounds Using Deep Learning," arXiv:1707.04642v2 [cs.SD], Oct. 19, 2017.

Rubin, J. et al., "Classifying heart sound recordings using deep convolutional neural networks and mel-frequency cepstral coefficients," in Computing in Cardiology Conference (CinC), 2016, 2016, pp. 813-816.

* cited by examiner ating a time-frequency representation of an electrocardiogram (ECG) signal acquired over a time interval; processing the time-frequency representation using a neural network (NN) to output probabilities for rhythms of a set of rhythms including at least atrial fibrillation; assigning a rhythm for the ECG signal based on the probabilities for the rhythms of the set of rhythms output by the neural network; and controlling a display device (24) to display the rhythm assigned to the ECG signal.

DETECTING ATRIAL FIBRILLATION USING SHORT SINGLE-LEAD ECG RECORDINGS

CROSS-REFERENCE TO PRIOR APPLICATIONS

This application is the U.S. National Phase application under 35 U.S.C. § 371 of International Application No. PCT/EP2018/075113, filed on Sep. 18, 2018, which claims the benefit of U.S. patent application Ser. No. 62/561,253, filed on Sep. 21, 2017. This application is hereby incorporated by reference herein.

FIELD

The following relates generally to the cardiac monitoring arts, electrocardiogram (ECG) monitoring and signal processing arts, atrial fibrillation detection arts; neural network processing arts, and related arts.

BACKGROUND

Atrial Fibrillation (AF) is the most common type of heart arrhythmia and its incidence in the United States alone is estimated to be 2.7-6.1 million people (see, e.g., C. T. January, L. S. Wann, J. S. Alpert, H. Calkins, J. C. Cleveland, J. E. Cigarroa, et al., "2014 AHA/ACC/HRS guideline for the management of patients with atrial fibrillation," Circulation, p. CIR. 0000000000000041, 2014). As such, AF screening using handheld easy-to-use devices has received a lot of attention in recent years.

There is a need for the development of ECG devices to classify normal sinus rhythm (NSR), AF, other rhythm (O), and noisy recordings from a short single-channel ECG recording (9-60 seconds). Most existing algorithms in ECG devices and/or bedside monitors need some time to adjust ECG data processing parameters and are not suitable for short ECG recordings.

Furthermore, most commercially available ECG devices are designed for acquiring and analysing multi-channel ECGs.

The following discloses new and improved systems and methods to overcome these problems.

SUMMARY

In one disclosed aspect, a non-transitory computer-readable medium stores instructions readable and executable by at least one electronic processor to perform an atrial fibrillation (AF) detection method. The method includes: generating a time-frequency representation of an electrocardiogram (ECG) signal acquired over a time interval; processing the time-frequency representation using a neural network (NN) to output probabilities for rhythms of a set of rhythms including at least atrial fibrillation; assigning a rhythm for the ECG signal based on the probabilities for the rhythms of the set of rhythms output by the neural network; and controlling a display device (24) to display the rhythm assigned to the ECG signal.

In another disclosed aspect, a device for detecting atrial fibrillation includes an ECG measurement device with one or more leads having one or more electrodes attachable to a patient. At least one electronic processor is programmed to: control the ECG measurement device to acquire an ECG signal over a single data acquisition time period and then to stop acquisition of the ECG signal; generate a time-frequency representation of an ECG signal acquired over a time interval with values of a time dimension indexing time windows of a sliding time window over the ECG signal and with, for each indexed time window, values along a frequency dimension representing a frequency spectrum of the portion of the ECG signal in the indexed time window; process the time-frequency representation using a neural network (NN) to output probabilities for rhythms of a set of rhythms including at least atrial fibrillation; assign a rhythm for the ECG signal based on the probabilities for the rhythms of the set of rhythms output by the neural network; and control a display device to display the rhythm assigned to the ECG signal.

In another disclosed aspect, an atrial fibrillation (AF) detection method (100) includes: acquiring an electrocardiograph (ECG) signal with an ECG measurement device; determining a signal quality index (SQI) of the ECG signal over the time interval; generating a time-frequency representation of an ECG signal acquired over a time interval with values of a time dimension indexing time windows of a sliding time window over the ECG signal and with, for each indexed time window, values along a frequency dimension representing a frequency spectrum of the portion of the ECG signal in the indexed time window; processing the time-frequency representation using a neural network (NN) to output probabilities for rhythms of a set of rhythms including at least atrial fibrillation, a normal sinus rhythm, another rhythm which is not a normal sinus rhythm and is not atrial fibrillation, and a noisy recording; assigning a rhythm for the ECG signal based on the probabilities for the rhythms of the set of rhythms output by the neural network; and controlling a display device to display the rhythm assigned to the ECG signal.

One advantage resides in determining atrial fibrillation in an ECG signal of short length.

Another advantage resides in providing a monitoring device that is well suited for providing atrial fibrillation screening using short duration ECGs.

Another advantage resides in providing a portable monitoring device that is well suited for providing atrial fibrillation assessment using short duration ECGs.

Another advantage resides in performing an initial signal quality assessment prior to transmitting ECG data to a cloud computing resource in order to avoid transmission/processing of unacceptably noisy ECG datasets.

Another advantage resides in using a neural network to assign rhythm types to ECG datasets.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION

Figure 1:
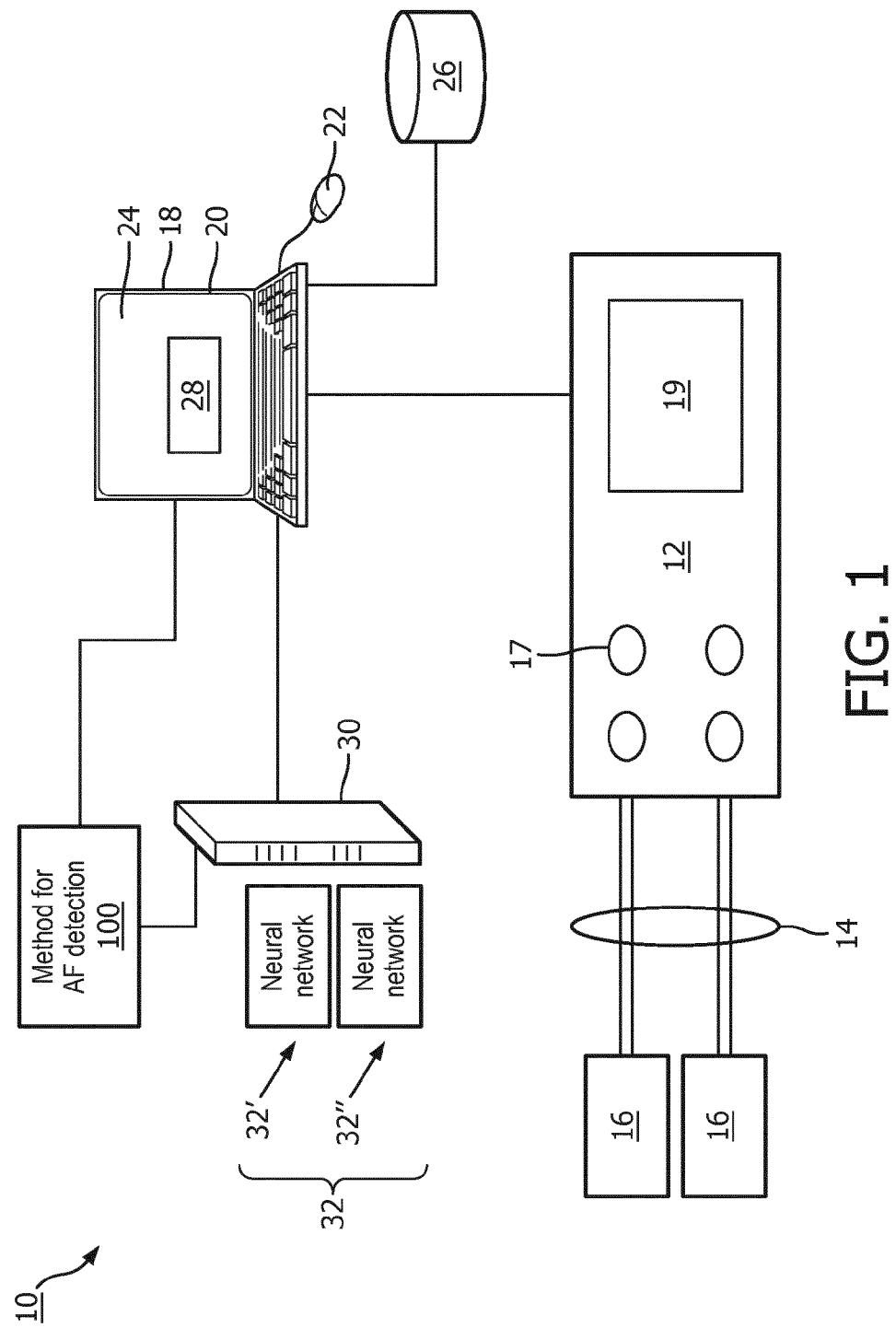
FIG. 1 diagrammatically shows an electrocardiogram (ECG) device for detecting atrial fibrillations according to one aspect.

The following relates to ECG devices capable of providing automated detection of atrial fibrillation in an ECG, which can be a challenging task, especially in the case of single-lead ECG (which employs only two electrodes). The disclosed approach converts the time-domain single-lead ECG to a two-dimensional (2D) time-frequency dataset using a sliding window. For each position of the sliding window (serving as the "x"-coordinate of the "2D representation"), a spectrum is computed (serving as the "y"-coordinate of the "2D representation"). In an illustrative example, a spectrogram is employed, but other frequency representations may be used such as a wavelet representation. The window size can be optimized at a 0.25 sec window size (corresponding to about one-quarter heartbeat). Such a time-frequency dataset can be analogized to a 2D "image", and image processing approaches can therefore be leveraged.

The 2D time-frequency dataset is compact and suitably processed using existing image processing paradigms. As disclosed herein, a neural network of a type designed to process images, such as a Convolutional Neural Network (CNN), can be employed to classify the ECG dataset in the 2D time-frequency representation. In some examples, a Densely Connected CNN (DenseNet; see, e.g., G. Huang et al., "Densely connected convolutional networks," arXiv preprint arXiv:1608.06993, 2016) concatenates all preceding layer feature-maps as input to the current layer, though other types of classifiers may be employed. The network can be trained on training samples each labeled by a clinician as one of four classes: "Normal Sinus Rhythm (NSR)"; "Atrial Fibrillation (AF)"; "Other Rhythms (O)"; or "Noise". The Noise label can be assigned if the clinician determined the ECG was too noisy to be reliably classified.

In a further variant, normalization can be performed between layers of the DenseNet. In some embodiments, this normalization is applied to one-dimensional columns (i.e. the frequency spectrum corresponding to each window position was separately normalized).

In some embodiments disclosed herein, a signal quality assessment is performed to generate a signal quality index (SQI) indicative of noise in the ECG dataset. In an illustrative SQI formulation, QRS detection is performed to segment the dataset into individual heart beats which are compared with a template, but other quality assessment approaches are contemplated. In a preferred implementation, the quality assessment is computationally fast and is performed locally, e.g. at the home heart monitoring device (or other ECG device), and only if the SQI is acceptable is the ECG dataset then transmitted to a cloud computing resource to perform the complex CNN-based classification. This approach improves efficiency by avoiding transmission/processing of unacceptably noisy ECG datasets. In the preferred embodiment, the CNN is trained to have a noise output thereby providing a second filter for discarding overly noisy ECG datasets. (It is also noted that employing cloud computing for the CNN-based classification is one suitable approach; it is alternatively contemplated to perform the CNN-based classification locally, e.g. at the home heart monitoring device if it has sufficient computing capacity).

In some actually performed tests, in instances in which the NSR or O classification has highest probability according to the CNN classifier, the NSR and O classification probabilities were similar. In other words, the CNN classified the ECG trace as NSR or O with high confidence, but provided low confidence for distinguishing between the NSR and O classifications. To overcome this problem, in some illustrative embodiments if the NSR and O probabilities were sufficiently similar then a different post-processing classifier was applied that was optimized to disambiguate the NSR and O classes. Similar post-processing could be used to disambiguate between other "close" classes.

In yet another embodiment, the signal analyses can be performed using two CNNs: a main CNN for ECG datasets with longer recording time, for example 15 seconds or longer, and a secondary CNN for shorter ECG datasets. In the illustrative examples, a main CNN processes 15 second segments, while a secondary CNN processes 9 second segments. An ensemble classifier that combines the results of the main and secondary CNNs is also contemplated, and would likely provide still further improved results. As a further variant, the ensemble classifier could additionally or alternatively include a CNN operating directly on the ECG dataset (in the time domain, rather than processing the 2D time-frequency dataset).

The disclosed ECG devices can employ single-shot ECG or continuous ECG monitoring. The single-shot ECG device would be particularly suitable for home monitors, and would be connected to the patient for a brief period in order to acquire the (single-shot) ECG dataset of 15 seconds or so, which would then be quality assessed and if acceptable uploaded to the cloud for ECG classification for example by using CNN classifier. The continuous ECG device is more suitable for continuous ECG monitoring in a hospital setting, and would classify successive 15 second ECG segments (possibly overlapping in time) to provide continuous ECG classification as to atrial fibrillation with low time latency.

With reference to FIG. 1, an illustrative device or system 10 for performing an atrial fibrillation (AF) detection is shown. As shown in FIG. 1, the system 10 includes an electrocardiogram (ECG) measurement device 12 with at least one lead 14 defined between two electrodes 16 attachable to a patient or held by a patient. The illustrative ECG device 12 is a single-lead ECG, which is commonly used for screening. However, the disclosed ECG analysis techniques can also be applied for multi-lead ECG such as a conventional 12-lead ECG of the type commonly used for diagnostic ECG. The ECG measurement device 12 can also include one or more buttons 17 for a user to edit settings of the ECG measurement device, and a screen 19 to display information related to the device and cardiac data from the patient. Still further, it is contemplated for the ECG device 12 to be embodied as a multi-function patient monitor that performs ECG monitoring along with other physiological monitoring functions (blood pressure, respiration, $SpO_2$, and/or so forth).

The device 10 may also include, or be otherwise connected with a workstation 18 comprising a computer or other electronic data processing device with typical components, such as at least one electronic processor 20, at least one user input device (e.g., a mouse, a keyboard, a trackball, and/or the like) 22, and a display device 24. It should be noted that these components can be variously distributed. For example, the electronic processor 20 may include a local processor of a workstation terminal and the processor of a server computer that is accessed by the workstation terminal. In some embodiments, the display device 24 can be a separate component from the computer 18. The workstation 18 can also include one or more databases or non-transitory storage media 26. The various non-transitory storage media 26 may, by way of non-limiting illustrative example, include one or more of a magnetic disk, RAID, or other magnetic storage medium; a solid state drive, flash drive, electronically erasable read-only memory (EEROM) or other electronic memory; an optical disk or other optical storage; various combinations thereof; or so forth. They may also be variously combined, e.g. a single server RAID storage. The display device 24 is configured to display a graphical user interface (GUI) 28 including one or more fields to receive a user input from the user input device 22. Some or all of the hardware shown as making up the workstation 18 may alternatively be integrated with the ECG device 12.

The illustrative workstation 18 is operatively connected with the ECG monitoring device 12 in order to receive an ECG data stream collected over a time period from the electrodes 16. This is often referred to as an ECG recording for the lead 14, and may for example be acquired for a fixed period of time such as 9 sec or 14 sec; or alternatively may be acquired continuously in the case of continuous patient monitoring. The ECG recording may be variously processed by the workstation 18 and/or preprocessed by electronics of the ECG measurement device 12 (such electronics not shown in FIG. 1) to perform various filtering or the like of the acquired counts data. In some embodiments, a cloud computer processor 30 employing a neural network (NN) 32 is programmed to further process the ECG signal to determine AF indications. In one example, the NN 32 can be a Convolutional NN (CNN). In another example, the CNN 32 can be a Densely Connected CNN, which, for each layer of the CNN, concatenates all preceding layer feature-maps as input (see, e.g., G. Huang, Z. Liu, K. Q. Weinberger, and L. van der Maaten, "Densely connected convolutional networks," *arXiv preprint arXiv:* 1608.06993, 2016).

The system 10 is configured to perform an AF detection method or process 100. To this end, the non-transitory storage medium 26 stores instructions which are readable and executable by the at least one electronic processor 20 of the workstation 18 to perform disclosed operations including performing the method or process 100 for performing AF detection. In some examples, the method 100 may be performed at least in part by cloud processing via the cloud computer processor 30, e.g. a cloud computing server (computer), network of servers, ad hoc network of servers, or so forth.

Figure 2:
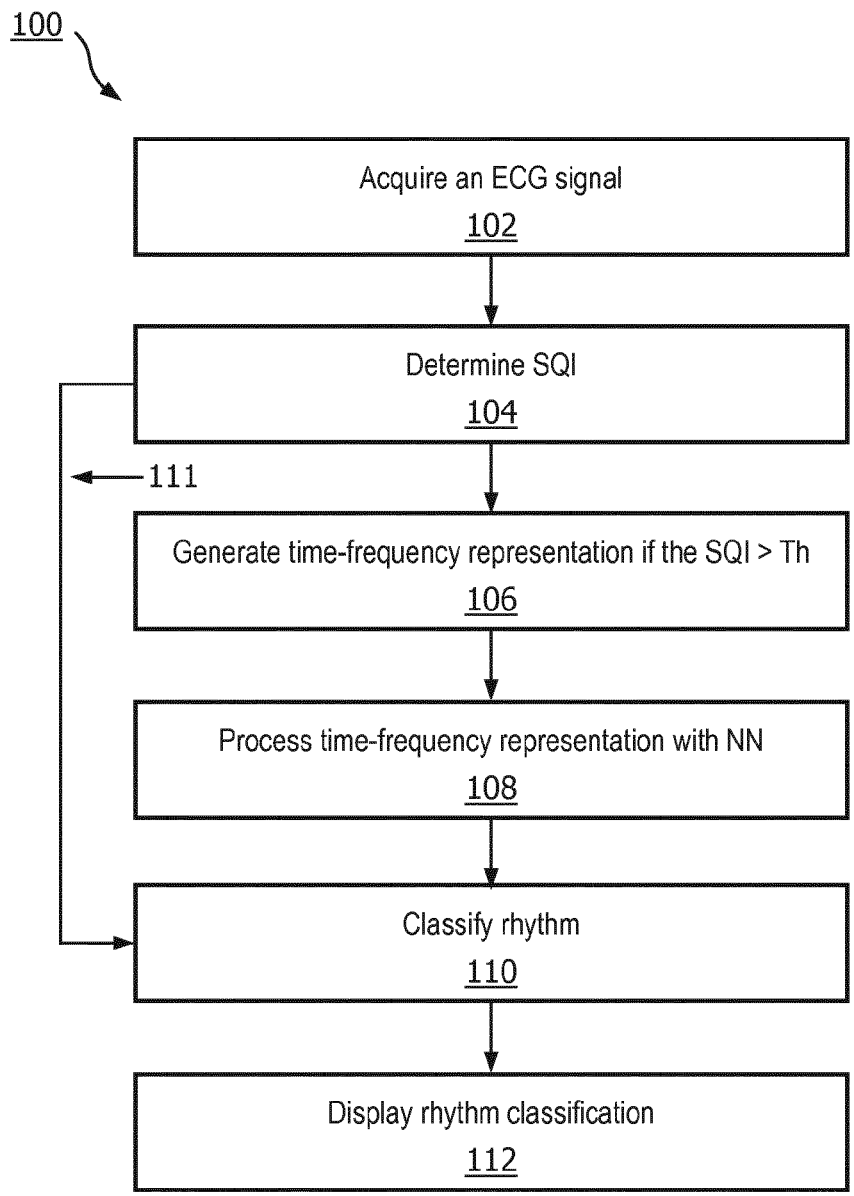
FIGS. 2 and 3 show exemplary flow chart operations of the ECG device of FIG. 1.

With reference to FIG. 2, an illustrative embodiment of the AF detection method 100 is diagrammatically shown as a flowchart. To begin the method 100, the electrodes 16 are attached to a portion of the patient's skin (e.g., on the arm, the chest, and so forth) or are hold by a patient, and are connected to the ECG measurement device 12 via wires to form the lead 14 of the illustrative single-lead ECG.

At 102, the at least one electronic processor 20 is programmed to control the ECG measurement device 12 to acquire an ECG signal over a time interval. In one example, the ECG signal is acquired over a single data acquisition time period. In some illustrative examples, the acquisition time period is 9 seconds, or 15 seconds, but substantially any acquisition time period may be employed. The at least one electronic processor 20 then controls the ECG measurement device 12 to stop acquisition of the ECG signal once the acquisition time period is complete. It is alternatively contemplated to employ continuous ECG recording in which the ECG signal is continuously acquired, and to apply the subsequent steps of the method 100 to a designated time interval of the continuously acquired ECG recording.

At 104, the at least one electronic processor 20 is programmed to determine a signal quality index (SQI) of the ECG signal over the time interval. To do so, the acquired ECG signal is processed to detect a QRS portion of the signal using a suitable algorithm. In some examples, the SQI can have a preselected SQI threshold of approximately 0.5. If the SQI is below the preselected SQI threshold, then the method 100 stops and the ECG signal is classified or determined to be noise. If the SQI is above the preselected SQI threshold, then the ECG signal is transmitted to the cloud computer processor 30 for further processing. The operation 104 advantageously identifies ECG recordings that are too noisy to be effectively classified before performing computationally expensive and bandwidth intensive processes of transmitting the data to the cloud and processing with the neural network 32; however, in other embodiments operation 104 is optionally omitted and the ECG data is transmitted to the cloud for processing without the quality check 104 and/or with SQI as one of input to the NN 32.

At 106, the cloud computer processor 30 is programmed to generate a time-frequency representation of the ECG signal. To do so, the cloud computer processor 30 is programmed to generate the time-frequency representation with values of a time dimension by indexing time windows of a sliding time window over the ECG signal and with, for each indexed time window, values along a frequency dimension representing a frequency spectrum of the portion of the ECG signal in the indexed time window. In one example, the time window can be indexed by storing a start time (or a starting sample) of time window with a predefined length measured in time (or number of samples). In another example, the index value can be a center time (or sample) of the time window. The index value can also be determined by any other suitable operation.

In some embodiments, the frequency spectrum of the portion of the ECG signal in the indexed time window is a spectrogram or wavelet spectrum. The spectrogram can be constructed by a Fast Fourier Transform (FFT) applied on a moving window with the length of 0.25 seconds and overlap of 80%. Signal segments are then extracted from the spectrogram beginning at each of the detected QRS peaks. For each position of the sliding window (serving as the "x"-coordinate of the "image"), a spectrum is computed (serving as the "y"-coordinate of the "image"). The window size can be optimized at a 0.25 sec window size (corresponding to about one-quarter heartbeat). The 2D time-frequency representation contains a column for each window of a 0.25 sec sliding window. So the data set has some number of positions along the time dimension (note that successive time windows may overlap in time), with each position having some number of points in the frequency dimension storing the spectrum of the 0.25 second segment of ECG data.

At 108, the cloud computer processor 30 is programmed to process the generated time-frequency representation using the NN 32 to output probabilities for rhythms of a set of rhythms. The set of rhythms can include one or more of: atrial fibrillation (AF); a normal sinus rhythm (NSR); another rhythm which is not a normal sinus rhythm and is not atrial fibrillation (O); or a noise rhythm or noisy recording (N). As used herein, the N rhythm constitutes an ECG signal that is too noisy to detect a particular rhythm, the rhythm is dominated by noise, and so forth.

In some embodiments, the processing includes choosing one or more NNs 32 for use in the processing on the basis of a time length of the ECG signal from at least two different neural networks respectively trained on sets of ECG signal segments of different time lengths. For example, a first NN 32' can be implemented to process "long" ECG signal time signals (e.g., 15 seconds or longer), and a second NN 32" can be implemented to process "short" ECG signal time signals (e.g., between 9 and 15 seconds). In an illustrative example, 9 seconds of ECG data at a heart rate of 72 beats/min (e.g., equal to 1.2 beats/second) contains 7.5 beats. Each window of the sliding time window is, for example, 0.25 sec, so each window is a fraction of a heart beat.

At 110, the cloud computer processor 30 is programmed to assign a rhythm for the ECG signal (that is, classify the ECG signal as to the type of rhythm) based on the probabilities for the rhythms of the set of rhythms output by the NN 32. In one approach, the rhythm type (AF, NSR, O, or N) with highest probability is selected as the classification of the ECG. However, this approach can lead to misclassification if two classes have very similar probabilities (so that the NN is not strongly discriminative between these two classes). In experiments, it was found that this was most often the case as between the NSR and O classes, where it was often observed that the NN 32 output similar probabilities for NSR and O. To resolve this ambiguity, in some embodiments responsive to the probabilities output by the NN 32 for the normal sinus rhythm and the other rhythm being within a similarity threshold of each other, the cloud computer processor 30 is programmed to apply a secondary classifier to select the rhythm for assignment from between the normal sinus rhythm and the other rhythm. In instances when the SQI is below the preselected SQI threshold as determined at the step 104, the assigning includes assigning a noisy recording for the ECG signal (diagrammatically indicated in FIG. 2 by connector 111 representing flow from the SQI assessment 104 to the classification 110 in this case). The rhythm assignment for the ECG signal is transmitted back to the workstation 18.

At 112, the at least one electronic processor 20 is programmed to control the display device 24 to display the rhythm assigned to the ECG signal. (In an alternative embodiment in which the workstation 18 is integrated with the ECG device 12, the display 24 may be a component of the ECG device 12).

Figure 3:
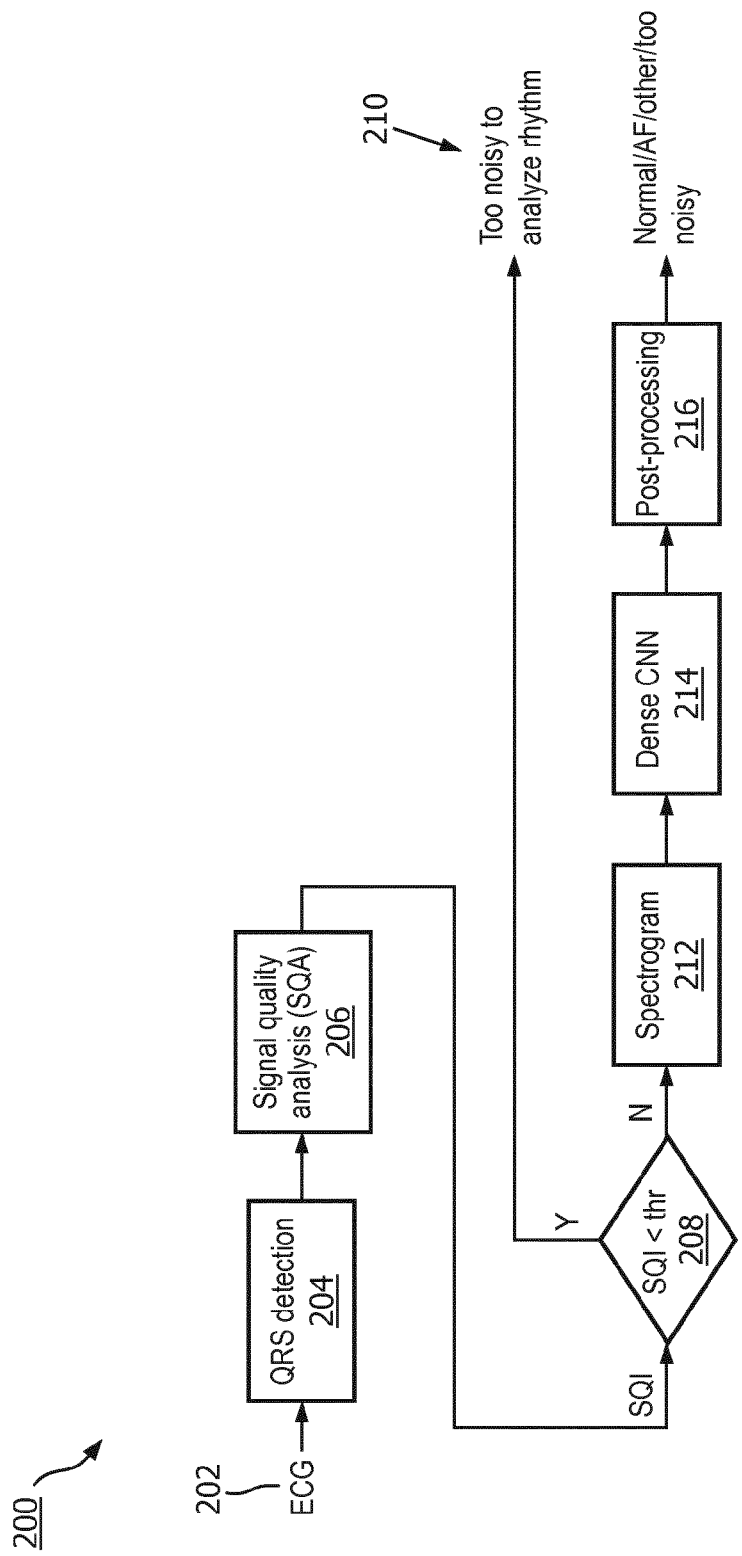

FIG. 3 shows another example of an AF detection method 200. At 202, an ECG signal is acquired. At 204, QRS portions of heart beats are detected in the ECG signal. At 206, SQI values based on QRS portions are determined. In some embodiments, operation 206 can also be performed before operation 204. At 208, the SQI values are compared to a threshold. At 210, if the SQI value is below the threshold, then the ECG signal is assigned as noise. At 212, if the SQI value is above the threshold, then a spectrogram of the ECG signal is generated. At 214, the spectrograms are analyzed by the NN 32, which in this embodiment is specifically a DenseNet, to assign probabilities of the ECG signal as AF, NSR, or O. At 216, optional post-processing is done, e.g. if the probabilities of two or more assignments for the ECG signal are within a similarity threshold, the ECG signal is post-processed by a classifier to determine the correct assignment for the ECG signal. As can be seen, the embodiment of FIG. 3 differs from that of FIG. 2 in that the embodiment of FIG. 3 specifically employs the DenseNet at 214, and the post-processing 216 may include other operations besides the secondary classifier.

EXAMPLE

The NN 32 of the cloud computing processor 30 requires training. In general, the training employs a training set of ECG recordings which are labeled as to rhythm type (AF, NSR, O, or noise). The labels of the training set may be provided manually, e.g. by having skilled cardiologists review the ECG recordings of the training set and assign the labels. The training of the NN 32 may employ any suitable neural network training approach to optimize the network, such as backpropagation of errors or the like.

For example, in some actually performed experiments, a training set for the NN 32 included 8,528 single-channel ECG recordings (NSR: 5050, AF: 738, O: 2456, and noise: 284). A 5-fold stratified split was applied to the 8,528 ECG recordings. Stratified splitting can be used to maintain class prevalence between the data splits. Recordings from four of the splits were used to construct a training/validation set (6821 ECG recordings) made up of the QRS aligned spectrogram segments. The training set included 80% of the above recordings. The other 20% were used as a validation set during model training. The remaining stratified split, consisting of 1,707 ECG recordings, was kept as an in-house test-set for assessing algorithm performance.

In another example, 6,312 30-second ECG segments representing atrial fibrillation were collected from various sources (including ambulatory recordings from Holter monitors) and used to augment the training and validation sets. Baseline wander segments was removed from each AF segment and up-sampled from 250 to 300 samples-per-second.

After removing baseline wander using a moving average filter, QRS complexes were detected using a GQRS algorithm, which is publicly available in WFDB toolbox for MATLAB. After aligning by the detected QRS peaks, an average template matching correlation coefficient with the threshold of 0.5 was used as the SQI to identify noisy data. This measure had the highest area under the receiver operating characteristic (ROC) curve for discriminating between artefacts and arrhythmic ECG.

For each recording, a spectrogram was constructed using an FFT applied on a moving window with the length of 75 samples and overlap of 80%. Segments with the length of 15 and 9 seconds were extracted from the spectrogram beginning at each of the detected QRS peaks.

If the quality of ECG recording was determined to be reasonable (such as SQI >0.5) by the SQI module, a rhythm classification was implemented using a dense convolutional neural network. Recordings processed by CNNs were classified as NSR, AF, O, as well as noisy. At first, a CNN model that processes 15-second segments was used. However, if the input recording length is not long enough, a secondary model that can process 9-second segments was used. The 15-second model as made up of 3 dense blocks consisting total of 40 layers. Each layer involves applying a convolutional filter, followed by ReLU activation and row-wise batch normalization. A growth rate of 6 feature-maps was used for each layer. Model input dimensions were a single channel of 20 frequency bins by 375 time segments. The first 20 frequency bins from the computed spectrogram captured a frequency range of up to approximately 50 Hz. In total, the model consisted of 262,344 trainable parameters. The architecture used for the secondary model was similar to the main model, however, a smaller growth rate of 4 feature-maps was used per layer. Model input dimensions were a single channel of 20 frequency bins by 225 time segments, height and width. The lower width resulting from the shorter 9-second segment size. In total, the secondary model consisted of 119,458 trainable parameters.

Both the main and secondary NN models were trained as four class classification models using standard Softmax cross-entropy loss. Models were typically trained for no more than 15 epochs. Once a model is sufficiently trained, in-house testing was performed on the left-out stratified split. Models that achieved desirable performance was further trained before submission to the challenge server. In particular, the full five splits of challenge data were used to train a final model, where 95% of the data was used for training and the remaining 5% for validation. Final model training did not occur from scratch, but rather weights from the previously learned model were used to pre-initialize the dense CNN for continued training using the updated, full dataset.

If the ECG is labelled as NSR or O by the CNN and the probability of being NSR and O are close to each other (absolute difference between probability of NSR and O<0.4), a feature-based post-processing step was performed to cast the final decision. For NSR/O post-processing, an Ada-Boost-abstain classifier was trained using the NSR and O recordings in the in-house training set.

In some examples, a total of 437 features were extracted from five different categories to train the model, including: (1) signal quality (2 features): average template matching correlation coefficient and bSQI based on the output of GQRS and Pan-Tompkins QRS detection algorithms; (2) frequency content (10 features): median power across nine frequency bands (1-15, 15-30, 30-45, 45-60, 60-75, 75-90, 90-150, 5-14, and 5-50 Hz) as well as ratio of power in 5-14 Hz band to power in 5-50 Hz (the power spectrum of the ECG record can be estimated using a discrete-time Fourier transform); (3) beat to beat interval (11 features): number, minimum, maximum, and median of RR intervals, SDNN, RMSSD, average heart rate, and different heart rate asymmetry measures (PI, GI, SI); (4) ECG-based reconstructed phase space (401 features) including normalized ECG reconstructed phase space (RPS) was created with dimension 2 and delay equal to 4 samples, in which the RPS can divided into small square areas (grid of 20×20) and normalized number of points in each square can considered a feature (in addition, a spatial filling index can be calculated); and (5) a Poincare section from ECG (13 features) using RPS reconstructed from ECG. 13 different features from Poincare section with unity line were extracted.

Performance of the NN 32 was evaluated using an average of three F1 values for classification of NSR, AF, and O ($F1_n$, $F1_a$, and $F1_o$, respectively). An in-house test set was also used for algorithm evaluation independent from the blind challenge test dataset. Also, performance was tested on a random subset of blind hidden test during official phase and final score was created using the whole blind test set.

An area under the ROC curve was determined for Ada-Boostabstain classifier in NSR/O post-processing step was 0.86 on the in-house test set. Only 58 features were selected by the classifier, including the top 10 from beat to beat interval (n=5), ECG-based reconstructed phase space (n=2), and Poincare section from ECG (n=3). Optimal results were achieved on the in-house test set was 0.82 (F1 for NSR, AF, and other rhythm were 0.90, 0.79, and 0.75, respectively), which are summarized in Table 1 below

TABLE 1

| Dataset | $F1_n$ | $F1_a$ | $F1_o$ | F1 |
|---|---|---|---|---|
| In-house test set | 0.91 | 0.80 | 0.76 | 0.82 |
| Subset of blind test set | 0.91 | 0.82 | 0.74 | 0.82 |

The performance of proposed NN 32 is four percent lower than top score (0.86).

The invention has been described with reference to the preferred embodiments. Modifications and alterations may occur to others upon reading and understanding the preceding detailed description. It is intended that the exemplary embodiment be construed as including all such modifications and alterations insofar as they come within the scope of the appended claims or the equivalents thereof.

The invention claimed is:

1. A device for electrocardiogram signal (ECG) processing, the device comprising:
   a single-lead electrocardiogram (ECG) measurement device operable to obtain a time-domain electrocardiogram signal (ECG) from a patient;
   at least one electronic processor programmed to carry out the steps of:
      receiving a time-domain electrocardiogram signal (ECG) from the single-lead ECG measurement device;
      determining a signal quality index (SQI) of the time-domain electrocardiogram signal (ECG) over a time interval;
      generating a time-frequency representation of the time-domain electrocardiogram (ECG) signal acquired over the time interval, by converting said time-domain electrocardiogram signal (ECG) to a two-dimensional time-frequency dataset using a sliding window;
      processing the time-frequency representation using a neural network to output probabilities for rhythms of a set of rhythms including at least atrial fibrillation;
      assigning a rhythm for the time-domain electrocardiogram signal (ECG) based on the signal quality index (SQI) and probabilities for the rhythms of the set of rhythms output by the neural network, wherein assigning includes assigning a noisy recording for the time-domain electrocardiogram signal (ECG) when the determined signal quality index (SQI) is below a preselected signal quality index threshold; and
      controlling a display device to display the rhythm or noisy recording assigned to the time-domain electrocardiogram signal (ECG).

2. The device of claim 1, wherein the set of rhythms includes at least:
   a normal sinus rhythm;
   atrial fibrillation; and
   other rhythms.

3. The device of claim 2, wherein the assigning includes:
   responsive to the probabilities output by the neural network for the normal sinus rhythm and the other rhythms being within a similarity threshold of each other, applying a secondary classifier to select the rhythm for assignment from between the normal sinus rhythm and the other rhythms.

4. The device of claim 1 wherein the set of rhythms includes at least:
   a normal sinus rhythm;
   atrial fibrillation; and
   a noisy recording.

5. The device of claim 1, wherein the processing includes choosing a neural network for use in the processing on the basis of a time length of the time-domain electrocardiogram signal (ECG) from at least two different neural networks respectively trained on sets of time-domain electrocardiogram signal (ECG) segments of different time lengths.

6. The device of claim 1, wherein the generating of the time-frequency representation of the time-domain electrocardiogram signal (ECG) comprises:
   generating the time-frequency representation with values of a time dimension indexing time windows of a sliding time window over the time-domain electrocardiogram signal (ECG) and with, for each indexed time window, values along a frequency dimension representing a frequency spectrum of the portion of the time-domain electrocardiogram signal (ECG) in the indexed time window.

7. The device of claim 6, wherein the frequency spectrum of the portion of the time-domain electrocardiogram signal (ECG) in the indexed time window is a spectrogram or wavelet spectrum.

8. The device of claim 1, wherein the processor does not perform the processing using the neural network if the determined signal quality index is below the preselected signal quality index threshold.

9. The device of claim 1, wherein the neural network is a convolutional neural network (CNN).

10. The device of claim 9, wherein the convolutional neural network is a Densely Connected convolutional neural network which, for each layer of the convolutional neural network, concatenates all preceding layer feature-maps as input.

11. The device of claim 1, wherein the processor is further programmed to carry out the step of:
controlling an electrocardiogram measurement device to acquire the ECG signal over a single data acquisition time period and then to stop acquisition of the time-domain electrocardiogram signal (ECG).

12. The device of claim 1, wherein the processor is further programmed to carry out the step of:
controlling an electrocardiogram measurement device to continuously acquire time-domain electrocardiogram signal (ECG) data;
wherein the time-domain electrocardiogram signal (ECG) acquired over the time interval is the segment of the continuously acquired time-domain electrocardiogram signal (ECG) data which is acquired over the time interval.

13. The device of claim 1, wherein the processor is further programmed to carry out the steps of:
performing the determining with at least one electronic processor; and assigning a rhythm of noise of the time-domain electrocardiogram signal (ECG) when the signal quality index (SQI) is below a preselected SQI threshold; and
when the signal quality index (SQI) is above the preselected SQI threshold, performing the generating, processing, and assigning with a cloud computing server.

* * * * *